United States Patent
Zibold et al.

(10) Patent No.: US 9,110,005 B2
(45) Date of Patent: Aug. 18, 2015

(54) STUD DETECTOR

(71) Applicant: Robert Bosch GmbH, Stuttgart (DE)

(72) Inventors: Tobias Zibold, Stuttgart (DE); Andrej Albrecht, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 129 days.

(21) Appl. No.: 13/888,090

(22) Filed: May 6, 2013

(65) Prior Publication Data

US 2013/0300436 A1 Nov. 14, 2013

(30) Foreign Application Priority Data

May 10, 2012 (DE) .......................... 10 2012 207 773

(51) Int. Cl.
*G01R 27/26* (2006.01)
*G01N 27/22* (2006.01)
*G01V 3/08* (2006.01)

(52) U.S. Cl.
CPC ............... *G01N 27/22* (2013.01); *G01V 3/088* (2013.01)

(58) Field of Classification Search
CPC .............................. G01N 27/22; G01V 3/088
USPC ................................................. 324/658–690
See application file for complete search history.

(56) References Cited

U.S. PATENT DOCUMENTS

| 4,099,118 A | 7/1978 | Franklin et al. |
| 5,812,057 A | 9/1998 | Hepworth et al. |
| 6,671,193 B1 * | 12/2003 | Pelkonen ..................... 363/53 |
| 2008/0175029 A1 * | 7/2008 | Jung et al. .................... 363/79 |
| 2008/0231292 A1 * | 9/2008 | Ossart et al. ................. 324/688 |

FOREIGN PATENT DOCUMENTS

| DE | 691 24 244 T2 | 8/1997 |
| DE | 197 38 391 A1 | 4/1998 |
| DE | 10 2007 041 612 A1 | 3/2009 |
| DE | 10 2008 054 445 A1 | 6/2010 |
| DE | 10 2010 028 718 A1 | 11/2011 |
| EP | 2 117 124 A1 | 11/2009 |

OTHER PUBLICATIONS

ISO124 Precision Low Cost Isolation Amplifier, 1997, available at http://www.ti.com/lit/ds/symlink/iso124.pdf.*
Kugelstadt, Industrial data-acquisition interfaces with digital isolators, 2011, available at http://www.ti.com/lit/an/slyt426/slyt426.pdf.*
Jones, Miniature solutions for voltage isolation, 2005, available at http://www.ti.com/lit/an/slyt211/slyt211.pdf.*

* cited by examiner

*Primary Examiner* — Melissa Koval
*Assistant Examiner* — Daniel Miller
(74) *Attorney, Agent, or Firm* — Maginot, Moore & Beck LLP

(57) ABSTRACT

A stud detector has a voltage source, a first device, and a second device. The first device serves to generate a voltage that is galvanically decoupled from the voltage source. The second device serves for the potential-free transmission of a control signal.

9 Claims, 2 Drawing Sheets

STUD DETECTOR

This application claims priority under 35 U.S.C. §119 to patent application no. DE 10 2012 207 773.1, filed on May 10, 2012 in Germany, the disclosure of which is incorporated herein by reference in its entirety.

BACKGROUND

Stud detectors (stud finders) for finding studs in light-frame construction walls are known from the prior art. Known stud detectors use a capacitive measuring method. This method generally detects a change in capacitance of one or a plurality of electrodes that arises if the electrode is near a stud that is arranged in a wall. This change in capacitance is, for example, detected by measuring a charging behavior of the electrode.

Known stud detectors are held against a wall that is to be examined by a user standing on a floor in front of a wall. It is known that walls, floors, and equipment users have a certain amount of conductivity, which allows an electrical current to flow from the stud detector via the wall, the floor, and the user back into the stud detector. Even if this conductivity and the resulting currents are small, these currents cause the measurement result to be skewed. In particular, the measurement result is skewed in such a way that when the stud detector approaches the wall, the capacitance of the one or a plurality of electrodes does not increase monotonically, as would be expected in the absence of current flow.

SUMMARY

The object of the present disclosure is to provide an improved stud detector. This object is achieved by means of a stud detector having the features described herein.

A stud detector according to the disclosure has a voltage source, a first device, and a second device. The first device serves to generate a voltage that is galvanically decoupled from the voltage source. The second device serves for the potential-free transmission of a control signal. This stud detector advantageously achieves galvanic isolation that makes it possible to reduce an electrical current flowing via a user of the stud detector significantly. In this way, skewing of a measurement result is advantageously prevented. This advantageously increases the measuring accuracy of the stud detector.

In a useful embodiment of the stud detector, the voltage source comprises a first battery. The stud detector can then be advantageously configured as a network-independent, portable device.

In one embodiment of the stud detector, the first device is configured to generate the galvanically decoupled voltage from a voltage provided by the voltage source. The first device comprises a light source and a solar cell or a heating element and a thermoelement or an electric motor and a generator or a transformer or a switching controller or a capacitor. The first device is thus advantageously suitable for providing the galvanically decoupled voltage with sufficient current-carrying capacity.

In a further development of the stud detector, the first device comprises a switching controller. The first device is configured to be operated in a burst mode. The switching controller then advantageously only has to be operated only for brief periods. During the remaining periods, a transformer of the switching controller can be completely decoupled via transistors, making it possible to achieve even more complete galvanic isolation.

In an alternative embodiment of the stud detector, the first device comprises a second battery. The second battery can particularly be configured as a button cell or as a similarly small battery. The second battery then advantageously has a small surface area and thus a low level of coupling relative to a hand of a user of the stud detector.

In a useful embodiment of the stud detector, the second device comprises an optocoupler. Optocouplers are advantageously ideally suited for the galvanically isolated transmission of control signals.

A further development of the stud detector has a third device that serves for the potential-free transmission of a measurement signal. Potential-free transmission of the measurement signal can then advantageously take place.

In a further development of the stud detector, the third device comprises an isolation amplifier. A measurement signal that is determined by means of the stud detector can then advantageously be transmitted and amplified in a galvanically isolated manner.

In a preferred embodiment of the stud detector, the isolation amplifier comprises an operational amplifier and a coupling capacitance. This advantageously constitutes a simple embodiment of the isolation amplifier that can be implemented in a cost-effective manner.

A preferred embodiment of the stud detector has at least one electrode, wherein the stud detector is configured to detect a change in capacitance of the electrode. The stud detector can then advantageously detect if a capacitance of the electrode changes due to a change in the dielectric in the vicinity of the stud detector, for example, by an approach of the electrode to an object. This makes it advantageously possible for the stud detector to detect the presence of the object.

BRIEF DESCRIPTION OF THE DRAWINGS

The disclosure will now be explained in detail by means of the accompanying Figures, in which.

DETAILED DESCRIPTION

Figure 1:
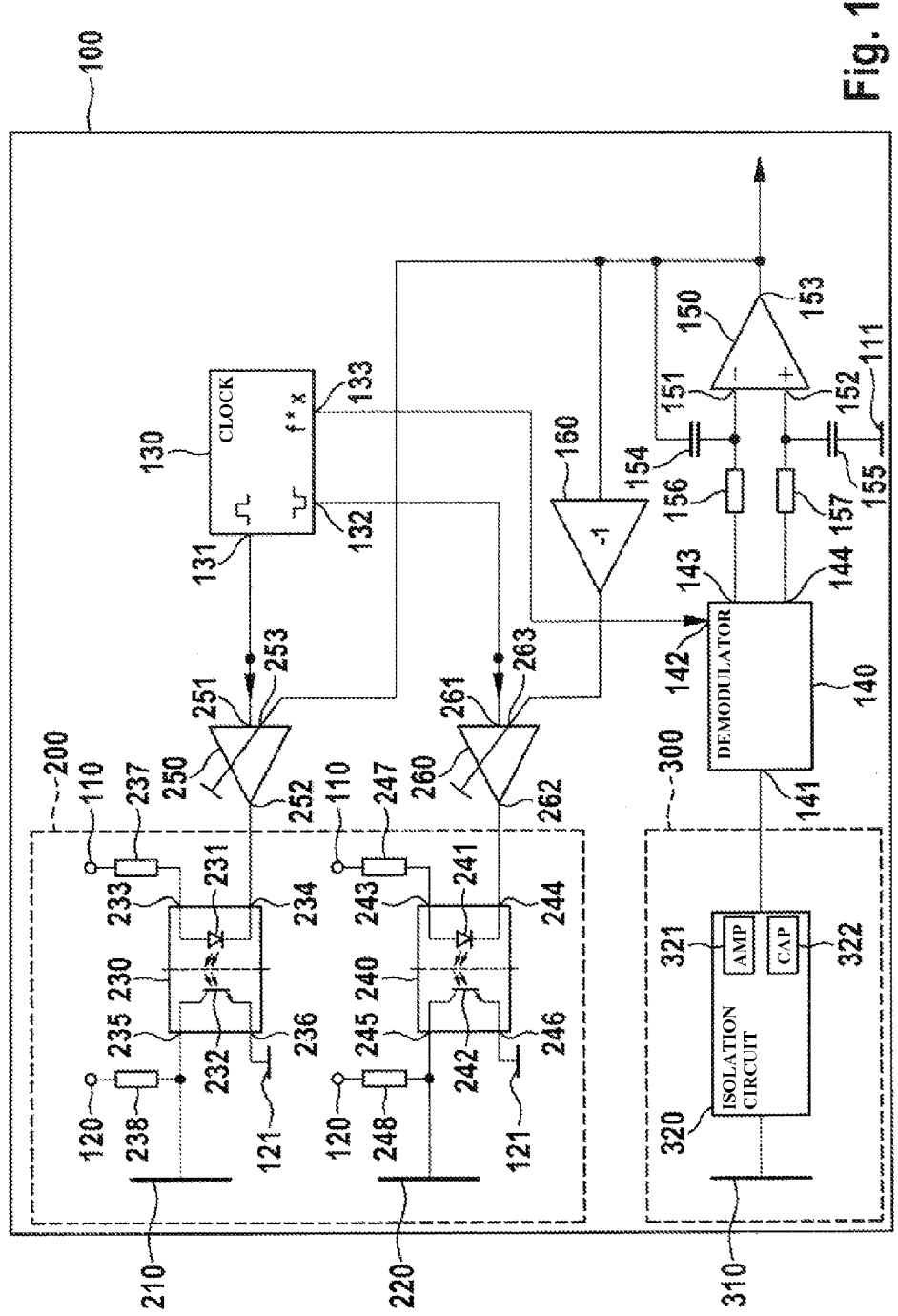
FIG. 1 is a switching arrangement of a stud detector according to an embodiment.

FIG. 1 shows a switching arrangement of a stud detector 100 according to an exemplary embodiment. The stud detector 100 can be used to find objects that are concealed from direct visibility. For example, the stud detector 100 can be used to find studs that are arranged in a lightweight-construction wall.

The stud detector 100 has internal galvanic isolation by means of which an electrical current flowing via a user of the stud detector 100 is substantially reduced. In particular, an electrical voltage in the stud detector 100 that is used for emitting a measurement signal is galvanically isolated relative to a voltage source of the stud detector 100. In addition, control and measurement information is transmitted in the stud detector 100 in a galvanically isolated manner.

The stud detector 100 that is illustrated by way of example works according to the measurement principle known from capacitive measuring technology of the so-called feedback amplifier with a synchronous demodulator. However, the stud detector 100 could also work in alternative embodiments according to any other measurement principle that uses at least one transmitting electrode and one receiving electrode or a combined transmitting and receiving electrode.

The stud detector 100 that is illustrated by way of example in FIG. 1 has two transmitting electrodes and one receiving electrode. However, other arrangements and numbers of electrodes would also be possible.

Figure 2:
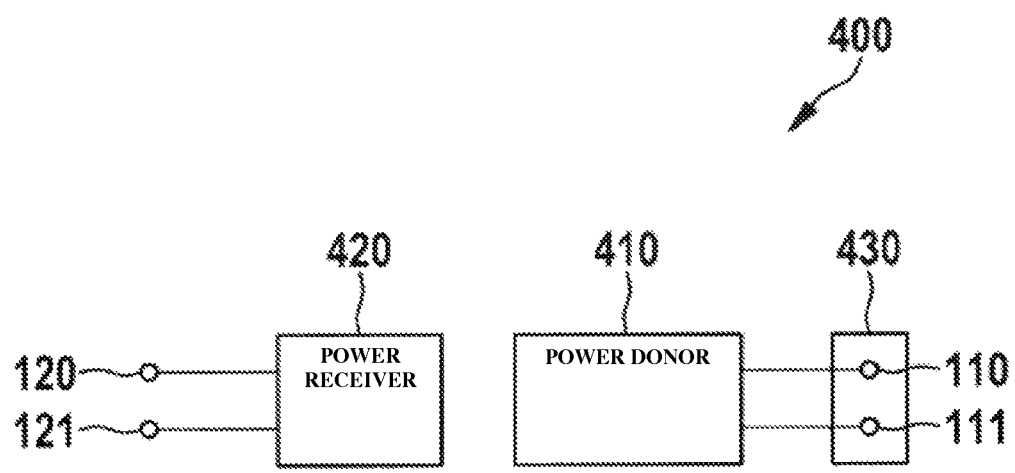
FIG. 2 is a block diagram of a device for generating a galvanically isolated voltage.

The stud detector 100 comprises a device 400 for generating a galvanically isolated voltage, which is not shown in detail in FIG. 1. This device 400 for generating a galvanically isolated voltage is shown in FIG. 2.

The stud detector 100 comprises a voltage source 430 that can be configured, for example, as a battery. Here, the term battery comprises both primary cells and rechargeable secondary cells (accumulators) and interconnections of such primary cells and secondary cells. The voltage source 430 provides a battery voltage 110 relative to a battery ground 111.

The device 400 for generating a galvanically isolated voltage serves to generate a galvanically isolated voltage 120 relative to a galvanically isolated ground 121 from the battery voltage 110 and battery ground 111 provided by the voltage source 430. For this purpose, in one embodiment, the device 400 comprises a power donor 410 and a power receiver 420 for generating a galvanically isolated voltage. The power donor 410 withdraws energy from the voltage source 430 and transmits it to the power receiver 420, thus ensuring galvanic isolation.

In one embodiment, the power donor 410 is a light source, for example, a light-emitting diode or a laser, and the power receiver 420 is a solar cell.

In another embodiment, the power donor 410 is a heating element and the power receiver 420 is a thermoelement.

In another embodiment, the power donor 410 is an electric motor and the power receiver 420 is a generator.

In another embodiment, the power donor 410 and the power receiver 420 are coil windings of a transformer.

In another embodiment, the power donor 410 and the power receiver 420 are coil windings of a galvanically isolated switching controller. In this embodiment, the switching controller can be configured to be operated in a burst mode, as the stud detector 100 has low overall power consumption. The switching controller can then be switched on only for a short period. In the remaining periods, a transformer of the switching controller can be completely decoupled via transistors, thus further improving the galvanic isolation of the device 400 for generating a galvanically isolated voltage.

In another embodiment of the device 400 for generating a galvanically isolated voltage, the power receiver 420 is a capacitor that can be connected to the voltage source 430 via a switch. The switch can, for example, be configured as a transistor. In order to charge the capacitor, the capacitor is connected via the switch to the voltage source 430. Charging preferably takes place as quickly as possible. The switch is then opened, thus separating the capacitor from the voltage source 430 and achieving galvanic isolation.

In an alternative embodiment of the device 400 for generating a galvanically isolated voltage, the galvanically isolated voltage 120 and the galvanically isolated ground 121 are provided by a second battery that is separate from the voltage source 430. This second battery can particularly be configured as a button cell or a similarly small battery. The second battery then has a small surface area and thus a low level of coupling relative to a hand of the user of the stud detector 100.

As can be seen in FIG. 1, the stud detector 100 has a transmitting portion 200 and a receiving portion 300. The transmitting portion 200 comprises a first transmitting electrode 210 and a second transmitting electrode 220. The receiving portion 300 comprises a receiving electrode 310.

The stud detector 100 comprises a clock generator 130 having a clock output 131, a push-pull output 132, and a modulation output 133. The clock output 131 is provided to output a clock signal having a specified frequency. The push-pull output 132 is provided to output a push-pull signal that is inverse to the clock signal that is output via the clock output 131. The modulation output 133 is provided to output a modulation signal that is dependent on the frequency of the clock signal that is output via the clock output 131.

The stud detector 100 furthermore comprises a first controllable amplifier 250 and a second controllable amplifier 260. The first controllable amplifier 250 has a signal input 251, a signal output 252, and a control input 253. The second controllable amplifier 260 has a signal input 261, a signal output 262, and a control input 263. The controllable amplifiers 250, 260 are configured to receive signals via the signal inputs 251, 261, amplify these signals, and then output them as amplified signals via the signal outputs 252, 262. The amplification factor can be adjusted via the control inputs 253, 263.

The signal input 251 of the first controllable amplifier 250 is connected to the clock output 131 of the clock generator 130. The signal input 261 of the second controllable amplifier 260 is connected to the push-pull output 132 of the clock generator 130.

The stud detector 100 furthermore has a first optocoupler 230 and a second optocoupler 240. The first optocoupler 230 comprises a light-emitting diode 231 that is arranged between a first input 233 and a second input 234 of the first optocoupler 230. The first optocoupler 230 also comprises a phototransistor 232 that is arranged between a first output 235 and a second output 236 of the first optocoupler 230. The second optocoupler 240 likewise comprises a light-emitting diode 241 that is arranged between a first input 243 and a second input 244 of the second optocoupler 240. The second optocoupler 240 also comprises a phototransistor 242 that is arranged between a first output 245 and a second output 246 of the second optocoupler 240.

The first input 233 of the first optocoupler 230 is connected to the battery voltage 110 via a first resistor 237. The second input 234 of the first optocoupler 230 is connected to the signal output 252 of the first controllable amplifier 250. The first output 235 of the first optocoupler 230 is connected to the galvanically isolated voltage 120 via a second resistor 238. The first output 235 of the first optocoupler 230 is also connected to the first transmitting electrode 210. The second output 236 of the first optocoupler 230 is connected to the galvanically isolated ground 121.

The first input 243 of the second optocoupler 240 is connected to the battery voltage 110 via a first resistor 247. The second input 244 of the second optocoupler 240 is connected to the signal output 262 of the second controllable amplifier 260. The first output 245 of the second optocoupler 240 is connected to the galvanically isolated voltage 120 via a second resistor 248. The first output 245 of the second optocoupler 240 is also connected to the second transmitting electrode 220. The second output 246 of the second optocoupler 240 is connected to the galvanically isolated ground 121.

The optocouplers 230, 240 thus work on the transmitting side using the voltage 110, 111 of the voltage source 430 of the stud detector 100. On the receiving side, the optocouplers 230, 240 work using the voltage 120, 121 that is galvanically isolated from the voltage source 430. The optocouplers 230, 240 serve for the potential-free transmission of control signals.

The stud detector 100 furthermore comprises a device 320 for the galvanically isolated transmission of a measurement signal, which is configured as an isolation amplifier in the embodiment in FIG. 1. The isolation amplifier 320 can, for example, have an operational amplifier 321 and a coupling capacitance 322.

The stud detector 100 furthermore comprises a synchronous demodulator 140 having a signal input 141, a modulation input 142, a first AC output 143, and a second AC output 144. The signal input 141 of the synchronous demodulator 140 is connected to the receiving electrode 310 via the isolation amplifier 320. The modulation input 142 of the synchronous demodulator 140 is connected to the modulation output 133 of the clock generator 130.

The stud detector 100 also has an integrating comparator 150 with an inverting input 151, a non-inverting input 152, and a differential output 153. The inverting input 151 of the integrating comparator 150 is connected to the first AC output 143 of the synchronous demodulator 140 via a first resistor 156. The non-inverting input 152 of the integrating comparator 150 is connected to the second AC output 144 of the synchronous demodulator 140 via a second resistor 157. The non-inverting input 152 is also connected to the battery ground 111 of the voltage source 430 via a second capacitor 155. The differential output 153 of the integrating comparator 150 is connected to the inverting input 151 of the integrating comparator 150 via a first capacitor 154. The differential output 153 of the integrating comparator 150 is also connected to the control input 253 of the first controllable amplifier 250. The differential output 153 of the integrating comparator 150 is also connected to the control input 263 of the second controllable amplifier 260 via an inverter 160.

The transmitting electrodes 210, 220 of the transmitting portion 200 are controlled by the clock generator 130 via the optocouplers 230, 240 in a push-pull manner, thus generating electrical fields. The amplitude of the push-pull control is separately determined for both transmitting electrodes 210, 220 via the controllable amplifiers 250, 260.

The receiving electrode 310 of the receiving portion 300 acts as a potential probe. The measurement signal that is received by the receiving electrode 310 is fed to the synchronous demodulator 140 via the isolation amplifier 320.

The gains of the controllable amplifiers 250, 260 and thus the amplitudes of the signals at the transmitting electrodes 210, 220 are adjusted such that the synchronous AC component at the receiving electrode 310 disappears. This condition is continuously sustained by the control circuitry formed from the synchronous demodulator 140 and the integrating comparator 150. The respective resulting control value is interpreted as the actual measured value.

In a simplified embodiment of the stud detector 100, it is possible to dispense with the galvanic isolation that is performed by the isolation amplifier 320 on the receiving side, since the receiving electrode 310 has only a slight coupling to the wall and to a hand of the user of the stud detector 100.

What is claimed is:

1. A stud detector comprising:
   a transmitting circuit having a first transmitting electrode configured transmit a first control signal, the first transmitting electrode being (i) connected to a voltage source via a galvanic isolation circuit and (ii) connected to a first signal input via a first potential-free transmission circuit, the galvanic isolation circuit being configured to galvanically isolate the voltage source from the first transmitting electrode, the first potential-free transmission circuit being configured provide the first control signal to the first transmitting electrode from the first signal input in a potential-free manner;
   a receiving circuit having a receiving electrode configured to receive measurement signals; and
   a measurement circuit configured to provide the first control signal to the first signal input of the transmitting circuit, receive the measurement signals from the receiving circuit, and detect whether a stud is present before the stud detector based on the measurement signals.

2. The stud detector according to claim 1, the transmitting circuit further comprising:
   a second transmitting electrode configured transmit a second control signal, the second transmitting electrode being (i) connected to the voltage source via the galvanic isolation circuit and (ii) connected to a second signal input via a second potential-free transmission circuit, the galvanic isolation circuit being further configured to galvanically isolate the voltage source from the second transmitting electrode, the second potential-free transmission circuit being configured provide the second control signal to the second transmitting electrode from the second signal input in a potential-free manner,
   wherein the measurement circuit is further configured to provide the second control signal to the second signal input of the transmitting circuit.

3. The stud detector according to claim 1, wherein the galvanic isolation circuit of the transmitting circuit comprises one of the following group: a light source and a solar cell; a heating element and a thermoelement; an electric motor and a generator; a transformer; a switching controller; and a capacitor.

4. The stud detector according to claim 3, wherein the galvanic isolation circuit of the transmitting circuit is a galvanically isolated switching controller configured to be operated in a burst mode.

5. The stud detector according to claim 1, wherein the first potential-free transmission circuit of the transmitting circuit is an optocoupler.

6. The stud detector according to claim 1, the receiving circuit further comprising:
   an isolation circuit configured to galvanically isolate the receiving electrode from an output of the receiving circuit.

7. The stud detector according to claim 6, wherein the isolation circuit of the receiving circuit is an isolation amplifier.

8. The stud detector according to claim 7, wherein the isolation amplifier includes an operational amplifier and a coupling capacitance.

9. The stud detector according to claim 1, wherein the measurement circuit is configured to detect whether a stud is present before the stud detector by detecting a change in capacitance of the receiving electrode of the receiving circuit.

* * * * *